United States Patent [19]

Meier

[11] Patent Number: 5,387,711
[45] Date of Patent: Feb. 7, 1995

[54] PROCESS FOR PREPARING 3-SULFOBENZOIC ACID AND ALKALI METAL SALTS THEREOF

[75] Inventor: Michael Meier, Frankfurt am Main, Germany

[73] Assignee: Hoechst AG, Frankfurt, Germany

[21] Appl. No.: 103,186

[22] Filed: Aug. 6, 1993

[30] Foreign Application Priority Data

Aug. 7, 1992 [DE] Germany ............... 4226131

[51] Int. Cl.$^6$ ........................................ C07C 303/22
[52] U.S. Cl. ........................................ 562/56
[58] Field of Search ........................................ 562/56

[56] References Cited

U.S. PATENT DOCUMENTS

| | | | |
|---|---|---|---|
| 1,676,698 | 7/1928 | Krecke | 562/56 |
| 2,642,458 | 6/1953 | Erickson et al. | 562/56 |
| 2,913,488 | 11/1959 | Blaser et al. | 562/56 |
| 3,636,016 | 1/1972 | McGuire et al. | 562/56 |
| 4,358,410 | 11/1982 | Demler et al. | 562/56 |
| 4,393,234 | 7/1983 | Blank et al. | 562/56 |
| 5,069,828 | 12/1991 | Dumas et al. | 562/56 |
| 5,136,043 | 8/1992 | Meier et al. | |
| 5,210,257 | 5/1993 | Harris | 562/56 |

FOREIGN PATENT DOCUMENTS

| | | | |
|---|---|---|---|
| 595720 | 4/1960 | Canada | 562/56 |
| 3122264 | 12/1982 | Germany . | |
| 3919840 | 1/1991 | Germany . | |
| 0083059 | 4/1988 | Japan | 562/56 |

OTHER PUBLICATIONS

Helvetica Chemica ACTA, Bd. 24, Nr. 2, 15, Mar. 1941, pp. 197–112.
Advanced Organic Chemistry, "Reactions, Mechanisms, and Structure", 3rd Edition, Jerry Mar. 1972, p. 444, Reaction O-117.
Offermann, H., *Liebigs Ann. der Chemie* 280(6):1–33 (1894).
Ruggli, P., et al., *Helv. Chem. Acta* 24:197–213 (1941).
Gilbert, E. E., et al., *Ind. a. Eng. Chem. vol.* 45:2065–2071 1953.

*Primary Examiner*—Marianne M. Cintins
*Assistant Examiner*—Keith MacMillan
*Attorney, Agent, or Firm*—Connolly and Hutz

[57] ABSTRACT

Process for preparing 3-sulfobenzoic acid and alkali metal salts thereof is disclosed. The present invention relates to a process for preparing 3-sulfobenzoic acid and/or alkali metal salts thereof, which comprises mixing 3-(chlorosulfonyl)benzoic acid with water and a water-immiscible solvent in which 3-sulfobenzoic acid is insoluble or only sparingly soluble, removing water from the mixture by azeotropic distillation, cooling and, if desired, admixing the 3-sulfobenzoic acid formed with alkali metal hydroxide and/or a substance forming alkali metal hydroxide and again removing water by azeotropic distillation.

19 Claims, No Drawings

PROCESS FOR PREPARING 3-SULFOBENZOIC ACID AND ALKALI METAL SALTS THEREOF

The present invention relates to a process for preparing 3-sulfobenzoic acid and/or alkali metal salts thereof, distinguished from the prior by a reduced production of effluent.

From Offermann, Liebigs Annalen der Chemie 280, 6 (1894), it is known that the sodium salt of 3-sulfobenzoic acid can be prepared by sulfonating benzoic acid with oleum at 200° C. pouring the resultant reaction product into a water-ice mixture and adding sodium chloride. A disadvantage of this process is that a dilute, sodium chloride-containing sulfuric acid is obtained, which can be worked up industrially only with great effort. Because of the high sodium chloride content the reaction product contains merely 75% of the sodium salt of the 3-sulfobenzoic acid.

In the process described in U.S. Pat. No. 4,358,410 benzoic acid is reacted with oleum at 130° C. and the reaction mixture obtained is subsequently admixed with a concentrated aqueous sodium chloride solution and cooled. This does lead to an improved purity of the product, but also to a large proportion of dilute sulfuric acid contaminated with sodium chloride, which is difficult to dispose of.

In a process described by Ruggli and Grün in Helv. Chim. Acta 24, 197 (1941) free 3-sulfobenzoic acid is obtained by reaction of 3-(chlorosulfonyl)benzoic acid with a 10-fold quantity of water while heating. Subsequently the water is distilled off, whereupon a syrup is obtained. This syrup is admixed with fresh water and the water subsequently distilled off again. This procedure is repeated twice. The disadvantage of this process is that three times large amounts of water, which cannot be used again, have to be distilled off. This requires a very high energy consumption. In addition, industrial implementation is only possible with difficulty, as 3-sulfobenzoic acid remains in the reaction vessel, which solid melts at 150° C. and therefore can only be removed from the reaction vessel as a hot melt. DE 3 122 264 and Ind. Eng. Chem. 45, 2065 (1953) relate to a process for preparing 3-sulfobenzoic acid by reaction of benzoic acid with the stoichiometric amount of sulfur trioxide. Here too, however, the solid product remaining in the reactor can only be removed in liquid melt form. This requires an increased technical effort and leads to problems in further processing. In addition, the handling of sulfur trioxide is not simple and requires special precautions.

There is therefore a need for a process which not only is simple to carry out technically, but also leads to a lowering of the amount of effluent. It should furthermore ensure that the desired product is obtained both in high yield and in high purity.

This object is achieved by a process for preparing 3-sulfobenzoic acid and/or alkali metal salts thereof, which comprises mixing 3-(chlorosulfonyl)benzoic acid with water and a water-immiscible solvent in which 3-sulfobenzoic acid is insoluble or only sparingly soluble, removing water from the mixture by azeotropic distillation, cooling and, if desired, admixing the 3-sulfobenzoic acid formed with alkali metal hydroxide and/or a substance forming alkali metal hydroxide and again removing water by azeotropic distillation.

The starting material 3-(chlorosulfonyl)benzoic acid can be prepared, for example, by the process described in DE 3 919 840. It can advantageously be used while moist with water. Its water content is usually from 20 to 40% by weight.

The process of the invention can be carried out both with comparatively very small and with relatively large quantities of water. Usually from 0.1 to 10, in particular from 0.3 to 4, preferably from 0.4 to 2 parts by weight of water are used per part by weight of 3-(chlorosulfonyl)benzoic acid.

A further feature of the process is the use of a water-immiscible solvent in which the 3-sulfobenzoic acid is insoluble or only sparingly soluble. It has proved advantageous to use an aromatic hydrocarbon for this.

Suitable solvents are, for example, toluene, mesitylene, o-xylene, m-xylene, p-xylene, mixtures of various xylenes, chlorobenzene and/or dichlorobenzene. Mixtures of the above solvents can also be used. Toluene and/or mesitylene, in particular toluene, can be used as solvent with good results.

Similarly well suited are o-xylene, m-xylene and/or p-xylene and their mixtures, in particular their technical grades.

Furthermore, chlorinated aromatic hydrocarbons, for example chlorobenzene and/or dichlorobenzene, in particular chlorobenzene, have proved usable solvents. However, any solvent can be used which is immiscible with water and serves as an azeotropic water-container, as long as it does not additionally dissolve the desired product, namely the 3-sulfobenzoic acid, or dissolves it only to a small extent. The abovementioned solvents are not a comprehensive list, but merely a selection of usable solvents.

The process can be performed with good results not only with the addition of comparatively low amounts of solvent, but also in the presence of relatively large amounts of solvent. Usually from 0.8 to 10, in particular from 1.5 to 3 parts by weight of solvent are used per part by weight of 3-(chlorosulfonyl)benzoic acid. It is nevertheless possible to work with lower or higher amounts of solvent than as specified above.

To carry out the process, 3-(chlorosulfonyl)benzoic acid is admixed with water and the solvent and vigorous mixing ensured. Subsequently the resulting mixture is heated to boiling and the water expelled by azeotropic distillation. The solvent in the distillate is separated off and returned to the azeotropic distillation.

The azeotropic removal of water can, alternatively, be carried out at reduced pressure, at atmospheric pressure or at superatmospheric pressure. The removal of water is particularly simple at atmospheric pressure. Therefore preference will frequently be given to this variant.

After all the water has been removed from the reaction mixture, i.e. no more water occurs as azeotrope, the suspension of solvent and crystallized 3-sulfobenzoic acid is cooled. Usually it is sufficient to employ a temperature from 40° to 5° C., in particular room temperature. Subsequently the crystallized 3-sulfobenzoic acid is separated off, for example by filtration or centrifugation, and dried if necessary.

The process is distinguished not only by a high yield, but also by a particular purity of the 3-sulfobenzoic acid. In particular the sulfobenzoic acid prepared in this way contains no chloride, for example in the form of alkali metal chlorides. The yield is >94% of theoretical. The 3-sulfobenzoic acid has a purity of >97%.

A particular advantage of the process is that the water separated off by azeotropic distillation can be used again for the hydrolysis of 3-(chlorosulfonyl)benzoic acid. This leads to a further reduction in the effluent produced in the reaction. In addition, it is only slightly contaminated by pollutants, particularly HCl. The usual occurrence of large amounts of dilute acid (aqueous sulfuric acid containing sodium chloride) is avoided and thereby the environmental pollution caused by effluent is considerably reduced.

Furthermore, it is surprising that the process of the invention, despite the expulsion of water at relatively high temperatures, does not lead to the elimination of water from the 3-sulfobenzoic acid formed and thus to the formation of the corresponding anhydrides.

If alkali metal salts of the 3-sulfobenzoic acid are to be prepared, this can involve either starting from already isolated and dried 3-sulfobenzoic acid prepared according to the invention or, advantageously, using the mixture obtained from the above-described preparation, which, after removal of water, is present as a suspension of 3-sulfobenzoic acid in the solvent. After reducing the temperature, for example to about 100° C. or below, this suspension can be reacted directly with alkali metal hydroxide or a substance forming alkali metal hydroxide, in particular an aqueous solution of the alkali metal hydroxide or the substance forming alkali metal hydroxide, and again distilling off the water azeotropically with the aid of the solvent. The alkali metal hydroxide used may be sodium hydroxide or potassium hydroxide. The substances forming alkali metal hydroxide may, for example, be alkali metal oxides, alkali metal carbonates or alkali metal hydrogen carbonates, in particular oxides, carbonates or hydrogen carbonates of sodium or potassium.

The process of the invention can be performed particularly simply with aqueous alkali metal hydroxide solutions. The aqueous solutions normally used contain from 5 to 50, in particular from 20 to 40% by weight of alkali metal hydroxide.

The mixture is heated and the water separated off as an azeotrope. The water separated off by distillation can be reused in the process without further treatment. It can be used either as a whole or in part in the hydrolysis step or can be used again for the preparation of the aqueous solution containing the alkali metal hydroxide or a substance forming alkali metal hydroxide. In this way the total amount of effluent per batch is again reduced.

After removal of the water by distillation, the suspension comprising the alkali metal salts of the 3-sulfobenzoic acid and solvent is cooled, usually to from 40° to 5° C., in particular to room temperature, the alkali metal salts are separated off, for example by filtration or centrifugation, and residual solvent is removed if necessary by washing, for example with acetone, metal ethyl ketone, n-propanol and/or isopropanol, and subsequent drying.

According to the invention alkali metal salts of the 3-sulfobenzoic acid which are free of alkali metal chlorides are obtained. The yield is above 93%. The purity of the desired product is at least 97%.

The following examples illustrate the invention, without limiting it.

Experimental part

EXAMPLE 1

Preparation of 3-sulfobenzoic acid 300 g of 3-(chlorosulfonyl)benzoic acid containing 38.8% water (corresponding to 183.6 g (0.83 mol) of 100% chlorosulfonylbenzoic acid) are admixed with 150 g of water and heated at 100° C. for 1 hour. Then 600 g of xylene are added dropwise over 1 hour and a total of 260 ml of water are azeotropically distilled off with xylene. The reaction mixture is cooled and the precipitate is filtered off with suction. After drying at 100° C./100 torr (13.16 kPa) 164.7 g of 3-sulfobenzoic acid are obtained, the purity determined by titration being 97.7%; this corresponds to a yield of 95.6%.

EXAMPLE 2

Preparation of 3-sulfobenzoic acid 300 g of 3-(chlorosulfonyl)benzoic acid containing 38.8% of water (corresponding to 183.6 g (0.83 mol) of 100% chlorosulfonylbenzoic acid) are admixed with 100 g of water and heated to 100° C. for 1 hour. Then 500 g of toluene are added dropwise over 1 hour and a total of 164 ml of water distilled off azeotropically with toluene. The reaction mixture is cooled and the precipitated product filtered off with suction. After drying at 100° C./100 torr (13.16 kPa) 163.5 g of 3-sulfobenzoic acid are obtained, the purity determined by titration being 98.2%; this corresponds to a yield of 95.4%.

EXAMPLE 3

Preparation of 3-sulfobenzoic acid 250 g of 3-(chlorosulfonyl)benzoic acid containing 35.9% of water (corresponding to 160.2 g (0.73 mol) of 100% chlorosulfonylbenzoic acid) are admixed with 86 g of water and 500 g of xylene and heated in a water separator. A total of 171 ml of water are expelled. The reaction mixture is cooled and the precipitated product filtered off with suction. After drying at 100° C./100 torr (13.16 kPa) 144.3 g of 3-sulfobenzoic acid are obtained, the purity determined by titration being 97.5%; this corresponds to a yield of 95.6%.

EXAMPLE 4

Preparation of sodium 3-sulfobenzoate 565.0 g of 3-(chlorosulfonyl)benzoic acid containing 32.9% water (corresponding to 379.1 g (1.72 mol) of 100% chlorosulfonylbenzoic acid) are admixed with 182 g of water and 1170 g of xylene and heated in a water separator. A total of 340 ml of water are distilled off azeotropically with xylene. After cooling the reaction mixture to 25° C. 210 g (1.73 mol) of 33% strength sodium hydroxide solution are added dropwise over 30 minutes. Subsequently another 170 ml of water are expelled. After cooling, the precipitated product is filtered off with suction. After drying at 100° C./100 torr (13.16 kPa) 370.2 g of sodium 3-sulfobenzoate are obtained, the purity determined by titration being 98.3%; this corresponds to a yield of 94.3%.

EXAMPLE 5

Preparation of sodium 3-sulfobenzoate 273.6 g of 3-(chlorosulfonyl)benzoic acid containing 28.6% water (corresponding to 195.3 g (0.89 mol) of 100% chlorosulfonylbenzoic acid) are admixed with 50 g of water and 500 g of chlorobenzene and heated in a water separator. A total of 106 ml of water are expelled. After cooling the reaction mixture to 100° C., 108 g (0.89 mol) of 33% strength sodium hydroxide solution are added dropwise over 30 minutes. Subsequently a further 90 ml of water are expelled. After cooling, the precipitated product is filtered off with suction. After drying at 100° C./100 torr (13.16 kPa) 190.4 g of sodium 3-sulfobenzoate are obtained, the purity determined by titration being 97.3%; this corresponds to a yield of 93.3%.

COMPARATIVE EXAMPLE 1

Preparation of sodium 3-sulfobenzoate according to U.S. Pat. No. 4,358,410

122.1 g (1.0 mol) of benzoic acid are melted at 125° to 130° C. in a 1 l four-neck flask fitted with stirrer, internal thermometer and reflux condenser. Then 405 g of oleum are introduced over 30 minutes. Subsequently the reaction mixture is heated to 130° C. and stirred for a further 1 hour at this temperature. The reaction mixture is cooled and 1800 g (=1500 ml) of 26.4% strength sodium chloride solution are run in over 15 minutes. The reaction mixture is heated to 80° C. to 85° C. Then the mixture is allowed to cool to 50° C. while stirring. Subsequently it is cooled with an ice bath to <5° C. and stirred for a further 30 minutes at this temperature. The precipitated product is filtered off with suction and washed with 256 g (=250 ml) of 5% strength sodium chloride solution cooled to 5° C., in two portions. After drying, 204.4 g of crude sodium 3-sulfobenzoate (content: 96%; sodium chloride content: 3%) are obtained; this corresponds to 196.3 g (0.88 mol) of sodium 3-sulfobenzoate calculated as 100%. 2342 g of effluent are produced.

COMPARATIVE EXAMPLE 2

Preparation of 3-(chlorosulfonyl) benzoic acid according to DE 39 19 840, Example 16

349.5 g=199.7 ml (3.0 mol) of chlorosulfuric acid and 20.0 g of 96% strength sulfuric acid are placed in a 2 l four-neck flask fitted with stirrer, internal thermometer, reflux condenser with gas outlet and dropping-funnel, at 25° C., and 1.0 g of sulfamic acid is added. Subsequently 122.1 g (1.0 mol) of benzoic acid are introduced into this mixture. The reaction mixture is heated to 120° C. over 3 hours and stirred further until evolution of HCl has ended (about 30 minutes). Then it is cooled to 70° C. and 119.0 g (1.0 mol) of thionyl chloride are added dropwise over 2 hours. The reaction solution is then heated to 80° C. and stirred further for about 30 minutes until gas evolution has ended. The mixture is added dropwise to 1000 g of ice-water at 10° C. over 2 hours. The precipitated product is filtered off with suction and washed with 500 g of ice-water. 321.2 g of crude 3-(chlorosulfonyl)benzoic acid (water content: 33.9%; chlorine: 10.8%) are obtained, corresponding to 212.3 g (0.96 mol) of 100% 3-(chlorosulfonyl)benzoic acid. 1115 g of mother liquor and 538 g of wash-water are produced.

As the summarized comparative presentation in the following table shows, the combination of the process described in DE 39 19 840 with the process of the invention, when compared with the prior art represented by U.S. Pat. No. 4,358,410, leads not only to a reduction in the amount of effluent, but also to a lowering of the wastes contained in the effluent.

Table

Comparison of the amounts contents of effluent produced in the preparation of 1 mol of sodium 3-sulfobenzoate, in each case starting with benzoic acid.

|  | 1*<br>Sodium 3-sulfobenzoate according to US 4 358 410 | 2*<br>Chlorosulfonyl-benzoic acid according to DE 39 19 840 | 3*<br>Hydrolysis according to Example 4 | 4*<br>sum of 2* and 3* |
|---|---|---|---|---|
| Amount of effluent: | 2674 g | 1818 g + | 314 g[1)] | 2132 g |
| $H_2SO_4$ | 371 g | 238 g + | — | 238 g |
| NaCl | 476 g | — + | — | |
| HCl | 41 g | 80 g + | 38.7 g | 118.7 g |

1* = Comparative example 1;
2* = Comparative example 2;
3* = Example 4;
4* = Sum of 2* + 3*
[1)]for the preparation of sodium 3-sulfobenzoate; in the preparation of 1 mol of 3-sulfobenzoic acid only 206 ml of water are produced.

What is claimed is:

1. A process for preparing 3-sulfobenzoic acid or alkali metal salts or mixtures thereof, which comprises mixing 3-(chlorosulfonyl)benzoic acid with water and a water-immiscible solvent in which 3-sulfobenzoic acid is insoluble or only sparingly soluble, removing water from the mixture by azeotropic distillation, cooling and optionally admixing the 3-sulfobenzoic acid formed with alkali metal hydroxide or a substance forming alkali metal hydroxide and again removing water by azeotropic distillation.

2. The process as claimed in claim 1, wherein from 0.1 to 10 parts by weight of water are used per part by weight of 3-(chlorosulfonyl)benzoic acid.

3. The process as claimed in claim 1, wherein the water-immiscible solvent used in which 3-sulfobenzoic acid is insoluble or only sparingly soluble is an aromatic hydrocarbon.

4. The process as claimed in claim 1, wherein the solvent used is toluene, mesitylene, o-xylene, m-xylene, p-xylene, chlorobenzene and/or dichlorobenzene.

5. The process as claimed in claim 1, wherein the solvent is toluene or mesitylene or a mixture thereof.

6. The process as claimed in claim 1, wherein the solvent used is o-xylene, m-xylene and/or p-xylene.

7. The process as claimed in claim 1, wherein the solvent is chlorobenzene or dichlorobenzene or a mixture thereof.

8. The process as claimed in claim 1, wherein from 0.8 to 10 parts by weight of solvent are used per part by weight of 3-(chlorosulfonyl)benzoic acid.

9. The process as claimed in claim 1, wherein the 3-sulfobenzoic acid formed is admixed with the equivalent amount of alkali metal hydroxide.

10. The process as claimed in claim 1, wherein the 3-sulfobenzoic acid formed is admixed with the equivalent amount of a substance forming alkali metal hydroxide.

11. The process as claimed in claim 2, wherein from 0.3 to 4 parts by weight of water are used per part by weight of 3-(chlorosulfonyl) benzoic acid.

12. The process as claimed in claim 2, wherein from 0.4 to 2 parts by weight of water are used per part by weight of 3-(chlorosulfonyl) benzoic acid.

13. The process as claimed in claim 5, wherein the solvent is toluene.

14. The process as claimed in claim 7, wherein the solvent is chlorobenzene.

15. The process as claimed in claim 8, wherein 1.5 to 3 parts by weight of solvent are used per part by weight of 3-(chlorosulfonyl) benzoic acid.

16. The process as claimed in claim 9, wherein the 3-sulfobenzoic acid formed is admixed with an equivalent amount of aqueous alkali metal hydroxide solution.

17. The process as claimed in claim 10, wherein the alkali metal hydroxide is an aqueous alkali metal hydrogen carbonate and/or an alkali metal carbonate solution.

18. The process as claimed in claim 1, wherein the 3-sulfobenzoic acid has a purity greater than 97% and has a theoretical yield of at least 94%.

19. The process as claimed in claim 1, wherein an aqueous alkali metal hydroxide solution contains from 5–50% by weight of alkali metal hydroxide.

* * * * *